(12) United States Patent
Yao et al.

(10) Patent No.: US 9,194,804 B2
(45) Date of Patent: Nov. 24, 2015

(54) STRESS ANALYSIS OF 3-D STRUCTURES USING TIP-ENHANCED RAMAN SCATTERING TECHNOLOGY

(71) Applicant: Taiwan Semiconductor Manufacturing Company, Ltd., Hsin-Chu (TW)

(72) Inventors: Liang-Gi Yao, Hsin-Chu (TW);
Yasutoshi Okuno, Hsin-Chu (TW);
Wei-Shan Hu, New Taipei (TW);
Yusuke Oniki, Hsin-Chu (TW);
Ling-Yen Yeh, Hsin-Chu (TW);
Clement Hsingjen Wann, Carmel, NY (US)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 16 days.

(21) Appl. No.: 14/017,079

(22) Filed: Sep. 3, 2013

(65) Prior Publication Data

US 2015/0062561 A1  Mar. 5, 2015

(51) Int. Cl.
*G01N 21/00* (2006.01)
*G01N 21/65* (2006.01)
*G01Q 30/02* (2010.01)

(52) U.S. Cl.
CPC ............... *G01N 21/65* (2013.01); *G01Q 30/02* (2013.01)

(58) Field of Classification Search
CPC .... H01J 37/32935; G01N 21/64; G01N 21/65; G01N 21/68; G01N 2015/1037; G01J 3/02
USPC .............................................. 356/72–73, 301
See application file for complete search history.

(56) References Cited

U.S. PATENT DOCUMENTS

2002/0159052 A1* 10/2002 Klooster et al. ............ 356/237.2
2007/0013907 A1*  1/2007 Pobortchi et al. ............. 356/301

* cited by examiner

*Primary Examiner* — Abdullahi Nur
(74) *Attorney, Agent, or Firm* — Slater & Matsil, L.L.P.

(57) ABSTRACT

A method includes performing a first probing on a sample integrated circuit structure to generate a first Raman spectrum. During the first probing, a first laser beam having a first wavelength is projected on the sample integrated circuit structure. The method further includes performing a second probing on the sample integrated circuit structure to generate a second Raman spectrum, wherein a Tip-Enhanced Raman Scattering (TERS) method is used to probe the sample integrated circuit structure. During the second probing, a second laser beam having a second wavelength different from the first wavelength is projected on the sample integrated circuit structure. A stress in a first probed region of the sample integrated circuit structure is then from the first Raman spectrum and the second Raman spectrum.

20 Claims, 7 Drawing Sheets

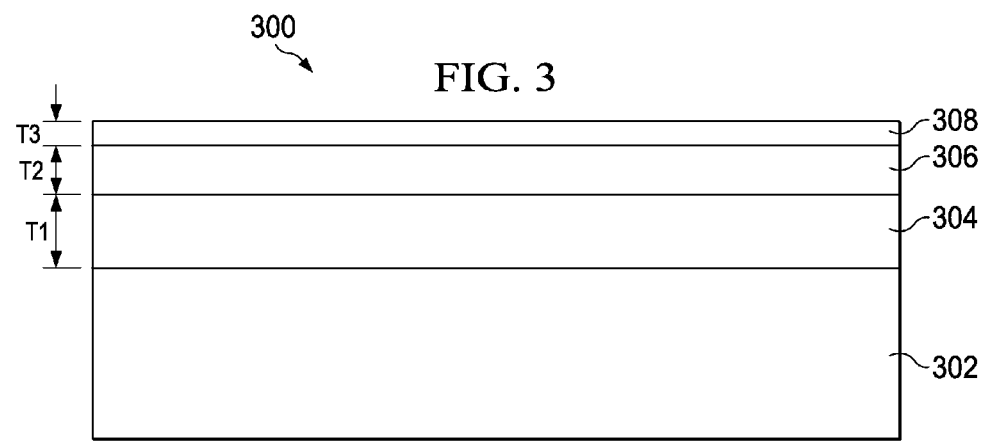
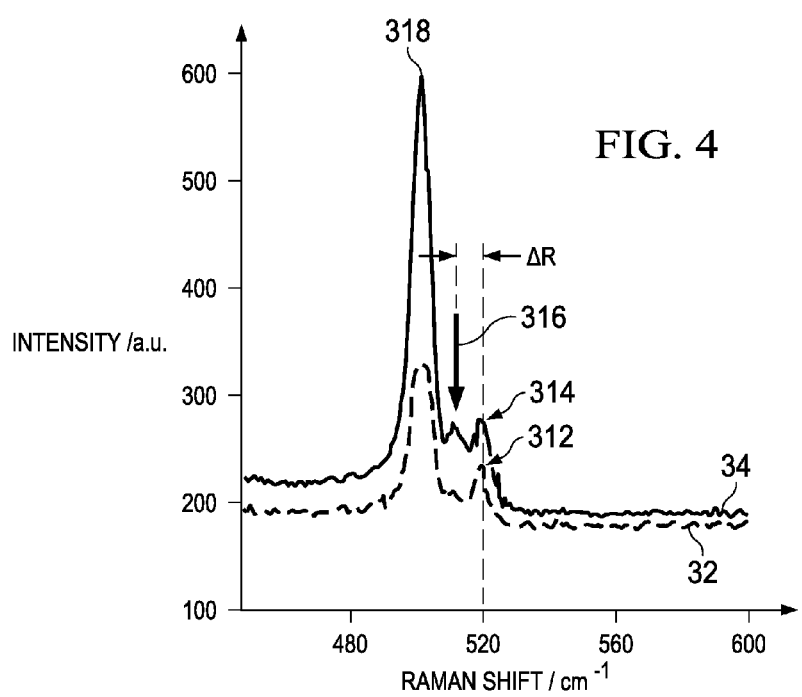

STRESS ANALYSIS OF 3-D STRUCTURES USING TIP-ENHANCED RAMAN SCATTERING TECHNOLOGY

BACKGROUND

The reduction in the size and the inherent features of semiconductor devices (e.g., a Metal-Oxide-Semiconductor (MOS) device) has enabled continued improvement in speed, performance, density, and cost per unit function of integrated circuits over the past few decades.

To enhance the performance of MOS device, stress may be introduced into the channel region of a MOS transistor to improve carrier mobility. Generally, it is desirable to induce a tensile stress in the channel region of an N-type Metal-Oxide-Semiconductor (NMOS) device in a source-to-drain direction, and to induce a compressive stress in the channel region of a P-type Metal-Oxide-Semiconductor (PMOS) device in a source-to-drain direction.

With the widely use of stresses for improving the performance of the MOS devices, it is important to be able to measure and analyze stresses. Particularly, with new channel materials such as germanium, silicon germanium, III-V compound semiconductors, and the like being more frequently used in three-dimensional (3D) structures, the stress analysis for the 3D structures becomes more important. Conventionally, the stress analysis was performed using Nano-Beam Diffraction (NBD) and micro-Raman microscopy.

BRIEF DESCRIPTION OF THE DRAWINGS

For a more complete understanding of the embodiments, and the advantages thereof, reference is now made to the following descriptions taken in conjunction with the accompanying drawings, in which:

FIG. 3 illustrates a cross-sectional view of a sample wafer including a plurality of layers over a substrate;

FIG. 4 illustrates the comparison of two Raman spectra obtained from the structure in FIG. 3, with one of the Raman spectra obtained using the far field Raman scattering, and the other obtained using Tip Enhanced Raman Scattering (TERS);

DETAILED DESCRIPTION OF ILLUSTRATIVE EMBODIMENTS

The making and using of the embodiments of the disclosure are discussed in detail below. It should be appreciated, however, that the embodiments provide many applicable concepts that can be embodied in a wide variety of specific contexts. The specific embodiments discussed are illustrative, and do not limit the scope of the disclosure.

A method of analyzing stresses in integrated circuit structures is provided in accordance with various exemplary embodiments. The intermediate stages of analyzing the stresses in accordance with an embodiment are illustrated. The variations of the embodiments are discussed. Throughout the various views and illustrative embodiments, like reference numbers are used to designate like elements.

Figure 1:
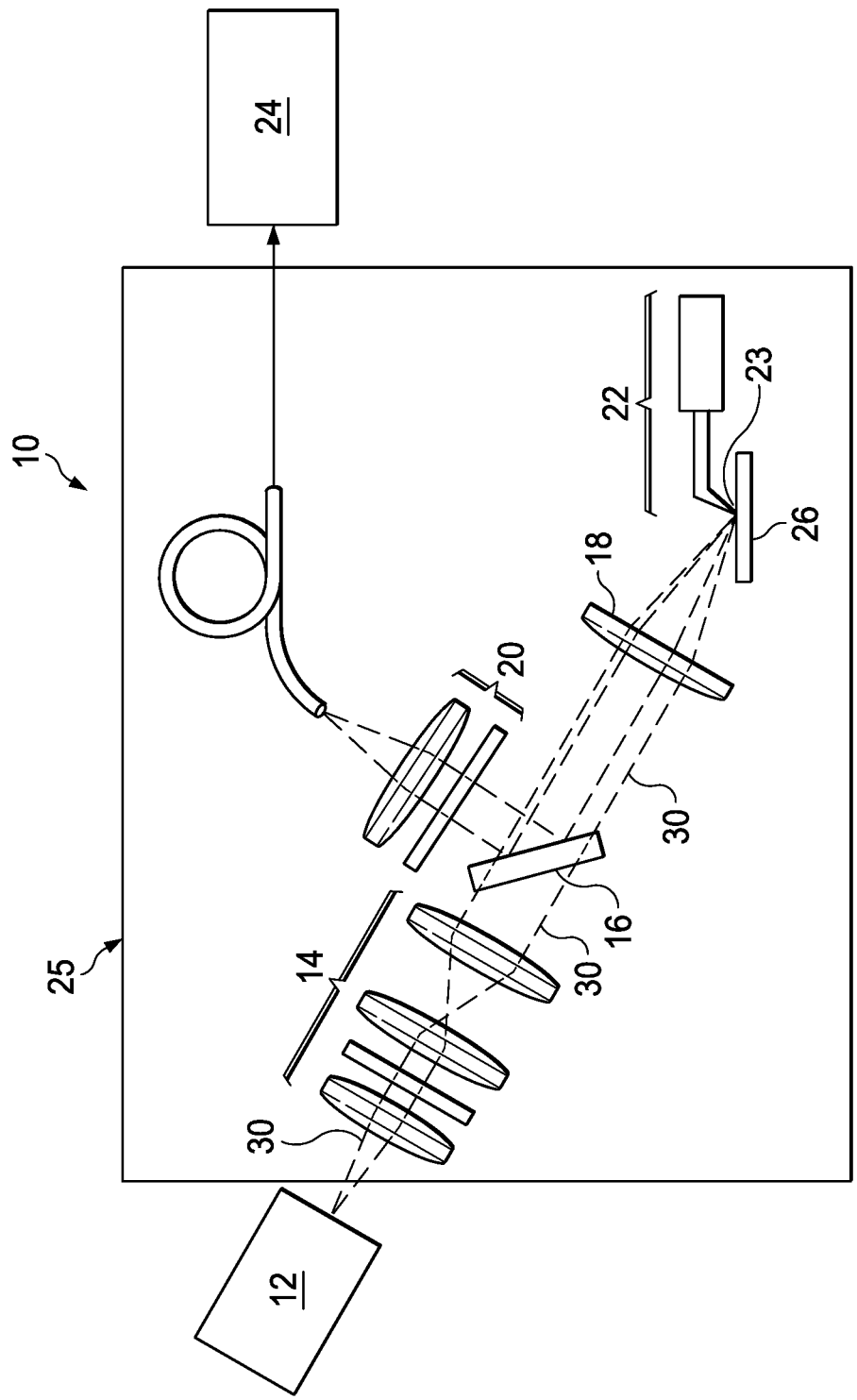
FIG. 1 illustrates an apparatus for performing Tip-Enhanced Raman Scattering (TERS) analysis on sample integrated circuit structures in accordance with embodiments.

FIG. 1 illustrates apparatus 10 for performing Tip-Enhanced Raman Scattering (TERS) probing and analysis on sample integrated circuit structures. In accordance with some exemplary embodiments, apparatus 10 includes multi-wavelength laser source 12, laser line filter 14, dichroic minor 16, objective lens 18, edge filter 20, Atomic Force Microscopy (AFM) probe 22, and spectrometer 24. It is appreciated that TERS probing apparatus 10 may have various design, and FIG. 1 illustrates an exemplary design. Multi-wavelength laser source 12 is configured to emit laser beam 30, and is configured to generate and emit a plurality of laser beams 30 that has a plurality of wavelengths. Laser line filter 14 is used to transmit laser and block all other light. Dichroic minor 16 allows laser beam 30 to pass through while reflects the Raman scattering signals obtained from the surface of sample 26 to spectrometer 24. Objective lens 18 is used to condense laser beam 30. Edge filter 20 allows Raman signals closer to the laser beam 30 to pass through.

Figure 10:
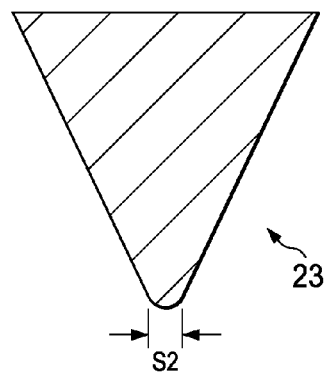
FIG. 10 illustrates a cross-sectional view of an Atomic Force Microscopy (AFM) probe tip.

AFM probe 22 comprises probe tip 23, which is schematically illustrated in FIG. 10. Probe tip 23 is used to scan the top surface of sample 26 (FIG. 1), wherein the scanning is synchronized with the projection of laser beam 30, so that probe tip 23 is close to where laser beam 30 is projected to. During the scanning, probe tip 23 and laser beam 30 move relative to sample 26. Accordingly, laser beam 30 and probe tip 23 may move together relative to sample 26, and laser beam 30 is projected to the same surface region (of sample 26) that probe tip 23 is nearby. As shown in FIG. 10, Tip 23 has a tip size S2 smaller than about 40 nm. The small tip size S2 enables the electrical field applied by AFM probe 22 to focus on a small region of sample 26, hence the planar resolution of the probing is improved, wherein the planar resolution is in the plane parallel to the surface of the respective sample. AFM probe 22 applies an electrical field to the underlying sample 26, which electrical field interacts with sample 26. Dipoles are thus generated in sample 26. The dipoles, when interacting with the injected laser beam 30, may cause the micro Raman scattering effect to be strengthened, and the Raman scattering signal intensity received by spectrometer 24 is increased.

Although FIG. 1 illustrates multi-wavelength laser source 12 as being a single unit, multi-wavelength laser source 12 may include a plurality of laser generators (not shown) therein, with each of the laser generators configured to generate the laser beam with one wavelength. Also, in some embodiments, laser line filter 14, dichroic mirror 16, objective lenses 18, edge filter 20, and the like may be shared by the laser beams having different wavelengths. In alternative embodiments, each of the plurality of laser beams may have its own laser line filter 14, dichroic minor 16, objective lenses 18, edge filter 20, and the like to suit to its wavelength.

FIG. 1 also illustrates chamber 25, in which the probing of sample 26 is performed. Sample 26, AFM probe 22, and some or all of laser line filter 14, dichroic mirror 16, objective lenses 18, edge filter 20 may be disposed in chamber 25. Chamber 25 may have a controlled environment to improve the probing. In accordance with some embodiments, when the TERS probing is performed, chamber 25 is vacuumed, for example, to a pressure smaller than about $10^{-6}$ Torr. In alternative embodiments, during the probing, chamber 25 is filled with an inert gas such as helium, argon, krypton, xeon, or the like. Controlling the ambient environment leads to a reduced interaction between laser beam 30 and sample 26, and hence the effect of AFM is more significant.

Figure 2A:
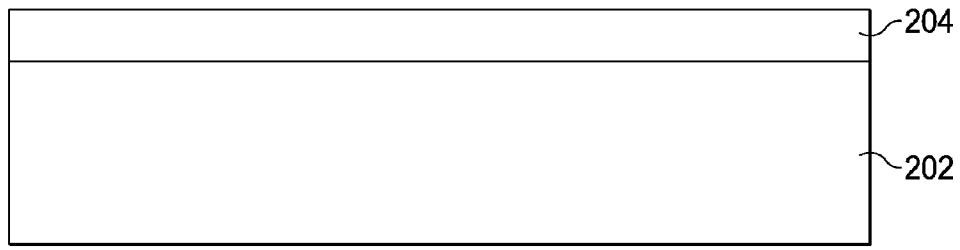
FIG. 2A illustrates a cross-sectional view of a sample wafer including a substrate and a silicon germanium layer over the substrate.

FIG. 2A illustrates the cross-sectional view of sample wafer 200, which includes bulk silicon substrate 202, and silicon germanium layer 204 on silicon substrate 202. The silicon germanium in silicon germanium layer 204 may be expressed as $Si_{1-x}Ge_x$, wherein x is the atomic percentage of germanium. A plurality of sample wafers 200 with the same structure as in FIG. 2A are provided, with the sample wafers having different germanium percentages "x."

Figure 2B:
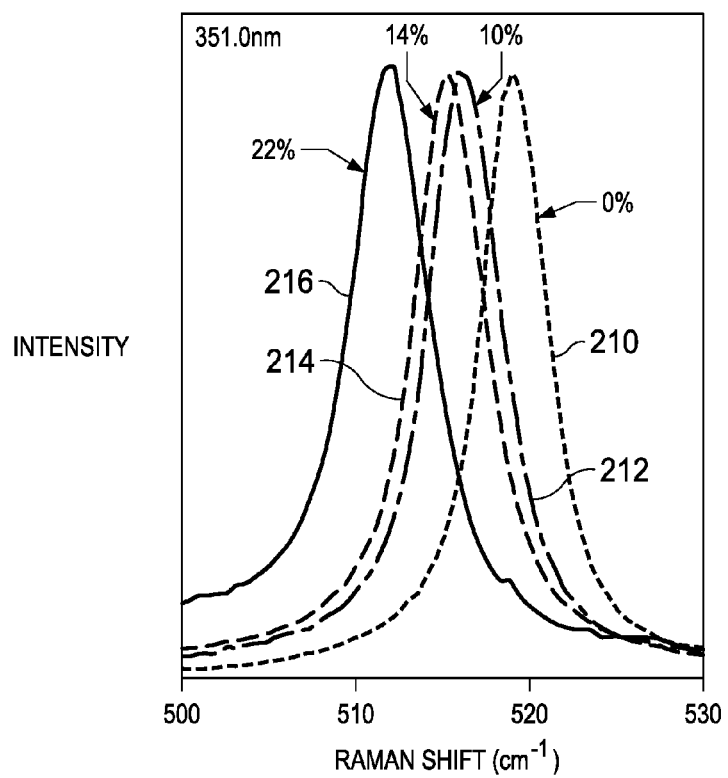
FIG. 2B illustrates a plurality of Raman spectra obtained using a plurality of sample wafers having the structure in FIG. 2A, wherein the silicon germanium layers in the sample wafers have different germanium percentages.

FIG. 2B illustrates the Raman spectra obtained from sample wafers 200, wherein the Raman scattering intensity is illustrated as a function of Raman shift. Spectrum 210 is the Raman spectrum of substrate 202, which has a germanium percentage of 0 percent. Bulk silicon substrate 202 does not have stress therein, and hence spectrum 210 is used as a reference Raman spectrum, to which other Raman spectra obtained from sample wafers are compared. Raman spectra 212, 214, and 216 correspond to the silicon germanium layers 204 (FIG. 2A) that have germanium percentages equal to 10 percent, 14 percent, and 22 percent, respectively. It is observed that the peaks of Raman spectra 212, 214, and 216 shift to the left of the peak in spectrum 210, and the greater the germanium percentages, the more the shifts are. Accordingly, FIG. 2B indicates that there is a direct relationship between the germanium percentages in layers 204 and the respective shift in the peaks of Raman spectra. Furthermore, the higher the germanium percentages, the higher the stresses in layers 204. By finding the magnitudes of the shifts of Raman peaks, the stresses in semiconductor wafers can be determined.

FIG. 3 illustrates sample wafer 300, which includes bulk silicon substrate 302 that is free from germanium. $Si_{1-y}Ge_y$ layer 304 is over substrate 302, wherein the germanium percentage y in layer 304 is equal to 0.025. Layer 304 is a buffer layer of the overlying layers. Thickness T1 of layer 304 is equal to about 0.2 µm. $Si_{1-z}Ge_z$ layer 306 is over layer 304, wherein germanium percentage z of layer 306 is equal to 0.25. Thickness T2 of layer 306 is equal to about 1 µm. Thin silicon layer 308 is formed over $Si_{1-z}Ge_z$ layer 306, and hence is a strained silicon layer. Thickness T3 of strained silicon layer 308 is equal to about 30 nm.

FIG. 4 illustrates two exemplary Raman spectra obtained from sample wafer 300 (FIG. 3), with one obtained from far field Raman Scattering (without tip-enhanced), and the other obtained using Tip Enhanced Raman Scattering (TERS) in accordance with the embodiments of the present disclosure. The signal intensity (the intensity of Raman scattering) is illustrated as Y axis, and is illustrated as a function of Raman shift (the X axis). Spectrum 32 represents the spectrum of a sample obtained using the far field Raman Scattering, and spectrum 34 represents the spectrum of the same sample obtained using TERS (enhanced by AFM). Spectrum 32 is obtained using a laser with a wavelength equal to about 577 nm or higher, and hence its penetration depth is at least deeper than about 1.1 µm. Accordingly, peak 312 of spectrum 32 reflects the stress corresponding to SiGe layer 304 or substrate 302 in FIG. 3. Since SiGe layer 304 has a very small germanium percentage, its peak is substantially merged with the peak of substrate 302, which is shown as peak 312.

It is observed from spectrum 32 that the peak of strained silicon layer 308 (FIG. 3) is not shown. This may be caused by the fact that the peak of strained silicon layer 308 is buried by the strong signal of layer 306. To bring up the peak of strained silicon layer 308, TERS is adopted to probe the same wafer 300. TERS is adopted in the embodiments for its better ability in revealing characteristic spectrum peaks than the conventional Raman Scattering analysis that does not include any AFM probe. The resulting Raman spectrum is illustrated as spectrum 34 in FIG. 4. TERS is capable of stimulate dipoles in shallow regions of the samples, and hence the peaks in shallow regions, for example, the regions with depth smaller than about 30 nm, are enhanced. As also shown in FIG. 4, spectrum 34 reveals characteristic spectrum peak 316 that is not revealed by spectrum 32, wherein characteristic spectrum peak 36 is generated by the Si—Si bonds in the strained silicon layer 308 in FIG. 3. In some embodiments, the generation of spectrum 34 is achieved using the laser that has the same wavelength as that is used for generating spectrum 32. In alternative embodiments, spectrum 34 may be generated using a laser with a wavelength shorter than the wavelength for generating spectrum 34. However, if a shorter-wavelength laser is used to generate spectrum 34, the heights of the peaks may be different from illustrated.

Peaks 314 and 312 have the same Raman shift values, regardless of whether spectra 32 and 34 are generated using lasers having the same wavelength or different wavelengths. Peak 316 is shifted from peaks 312 and 314 by ΔR. By determining the magnitude of ΔR, the stress value in strained silicon layer 38 can be determined, for example, using the relationship revealed by FIG. 4.

Conventional TERS system provides lasers with long wavelengths, for example, as long as 532 nm or even longer. Due to the high penetration depth of the laser with such long wavelength, the conventional TERS system can only enhance the intensity of samples in the depths of sub-micron range, for example, about 1 µm and deeper. Some integrated circuit structures (such as Fin Field-Effect Transistors (FinFETs)), however, are at the very shallow regions of the respective wafers, and the features to be analyzed may have the depth several nanometers. Therefore, the conventional TERS systems adopting lasers having long wavelengths are not suitable for analyzing such shallow integrated circuit structures.

Figure 5:
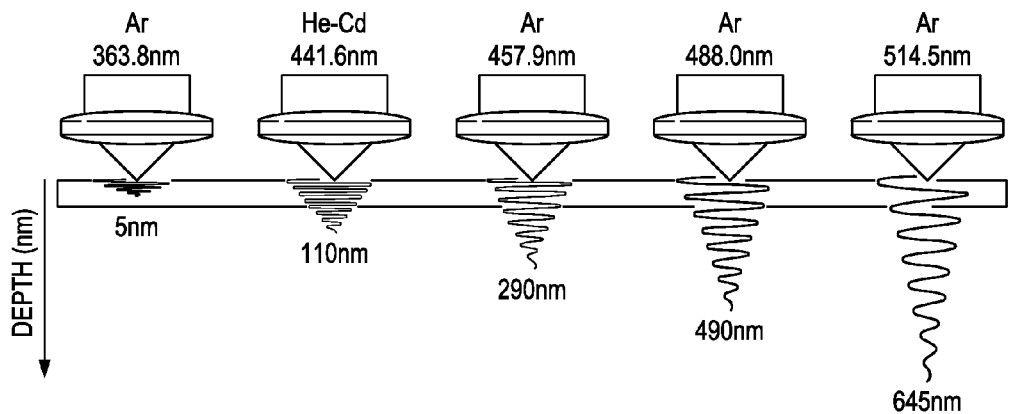
FIG. 5 illustrates a plurality of types of lasers and the respective penetration depths for the lasers to penetrating into samples.

FIG. 5 illustrates the relationship between the wavelengths of some exemplary lasers and the corresponding penetration depths into sample integrated circuit structures. The illustrated lasers include an argon laser having a wavelength of 363.8 nm, a He—Cd laser having a wavelength of 441.6 nm, an argon laser having a wavelength of 457.9 nm, an argon laser having a wavelength of 488 nm, and an argon laser having a wavelength of 514.5 nm. FIG. 5 indicates that with the increase in the wavelengths of the lasers, the penetration depths increase correspondingly. For example, the lasers having wavelengths of 363.8 nm, 441.6 nm, 457.9 nm, 488 nm, and 514.5 nm have the penetration depths up to about 5 nm, 110 nm, 290 nm, 490 nm, and 645 nm, respectively. The lasers that can be used include visible-light lasers (with wavelengths in the range between about 400 nm and about 760 nm) and lasers out of the visible-light range. Among the illustrated exemplary lasers, the laser with the wavelength of 363.8 nm is an ultraviolet laser, and the lasers with the wavelengths of 441.6 nm, 457.9 nm, 488 nm, and 514.5 are visible-light lasers. Although not illustrated, other lasers with different wavelengths than what are illustrated can be used (which may also include infrared-light lasers) may also be generated by multi-wavelength laser source 12 (FIG. 1) and used in the embodiments in addition to the illustrated lasers. It is appreciated that the term "penetration depths" means the depth that the laser can reach, and within which the Raman scattering has a detectable strength. In the regions of the sample integrated circuit structure deeper than the penetration depths, the respective Raman scattering will be too weak to detect. Accordingly, the penetration depths are affected by the capability of apparatus 10 (FIG. 1) and the wavelengths of the respective lasers.

Figure 6:
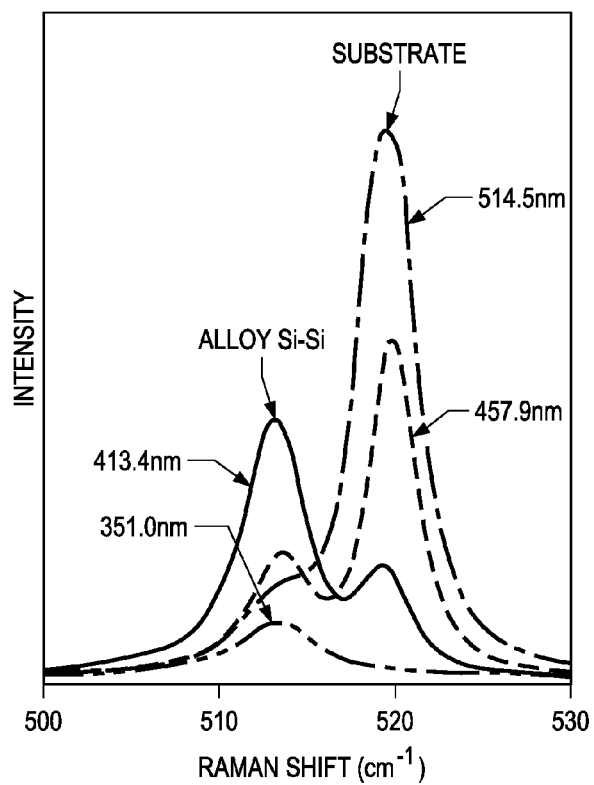
FIG. 6 illustrates a plurality of Raman spectra obtained from a same sample integrated circuit structure using different light wavelengths.

FIG. 6 illustrates a plurality of Raman spectra obtained from a same sample (not shown), while a plurality of light sources (such as lasers) with different wavelengths is used. Each Raman spectrum in FIG. 6 is generated from one of the plurality of light sources. Exemplary wavelengths of the light sources are marked, which include 351.0 nm, 413.4 nm, 457.9 nm, and 514.5 nm. The results indicate that regardless of the wavelengths of the light sources, the positions of the Raman characteristic peaks remain at the same locations, such as at about 512/cm and about 520/cm. This provides the possibility of obtaining stresses at different depths using different wavelengths, as used by the embodiments of the present disclosure.

In subsequent paragraphs, some exemplary process steps for determining stresses are discussed. Referring back to FIG. 1, in accordance with some embodiments, multi-wavelength laser source 12 is configured to generate a plurality of laser beams 30 (at different times) that have different wavelengths. Each of the laser beams 30 generated by multi-wavelength laser source 12 is projected on the same sample 26 (FIG. 7) to generate a Raman spectrum, and the Raman spectrums obtained from the lasers having different wavelengths are compared to obtain stress information in sample 26.

Figure 7:
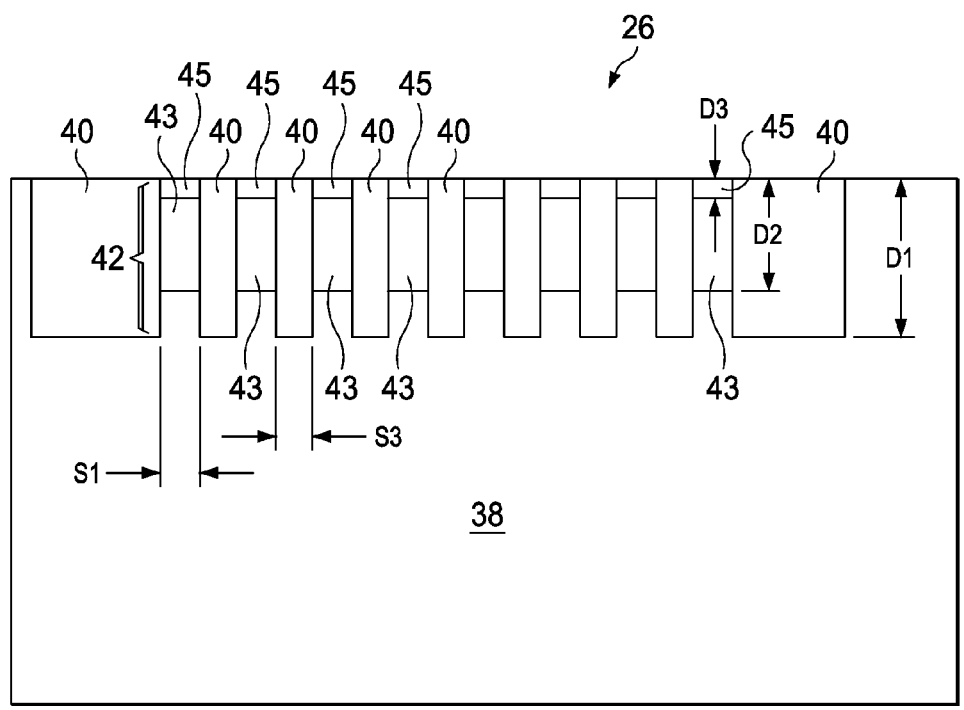
FIG. 7 illustrates a cross-sectional view of a sample integrated circuit structure in accordance with some embodiments, which includes semiconductor materials between Shallow Trench Isolation (STI) regions.

FIG. 7 illustrates a cross-sectional view of sample 26, which is probed using the TERS in accordance with the embodiments of the present disclosure. Sample 26 includes substrate 38, which may be a silicon substrate, a silicon carbon substrate, a III-V compound semiconductor substrate, or the like. Shallow Trench Isolation (STI) regions 40 are formed in substrate 38, and extend from a top surface of substrate 38 into substrate 38 for a depth marked as D1. Semiconductor regions 42 are located between STI regions 40. Semiconductor regions 42 comprise epitaxy semiconductor regions 43. Epitaxy semiconductor regions 43 are formed of a semiconductor material different from that of substrate 38, and may include silicon germanium, a III-V compound semiconductor, or the like. In an exemplary embodiment, semiconductor regions 43 comprise silicon germanium. Strained silicon layer 45 is formed over each of epitaxy semiconductor regions 43. Strained silicon layer 45 may be free or substantially free from germanium. In the embodiments semiconductor regions 43 comprises silicon germanium, the stress in regions 40, 42, and 43 may be affected by the percentage of germanium in regions 43, with higher germanium percentages corresponding to higher stresses. The distance between neighboring STI regions 40 are marked as S1. In an exemplary embodiment, distance S1 is in the range between about 3 nm and about 200 nm, and depth D1 is smaller than about 200 nm. Furthermore, depth D2 of regions 43 may be equal to or smaller than depth D1. In some embodiments, depth D3 of strained silicon layer 45 is between about 0.5 nm and about 3 nm, and depth D2 is between about 15 nm and about 50 nm, although different depths may also be used. It is appreciated that samples 26 with different S1, D1, D2, and D3 values may also be probed for determining the respective stress values. However, if values S1, D1, D2, and D3 are different from those in the discussed-examples, the wavelengths of the respective lasers need to be changed accordingly.

In the above-discussed embodiments, referring back to FIG. 1, a first probing is performed, wherein multi-wavelength laser source 12 generates laser beam 30 that has a first wavelength. The first wavelength has a respective penetration depth greater than depth D1 in FIG. 7. For example, the first wavelength may be 457.9 nm, 488 nm, or 514.5 nm. Accordingly, the first laser beam 30 may penetrate into sample 26 and reach the bulk substrate 38. As a result, the respective Raman spectrum may reveal the stress information in the bulk regions below STI regions 40.

Figure 8A:
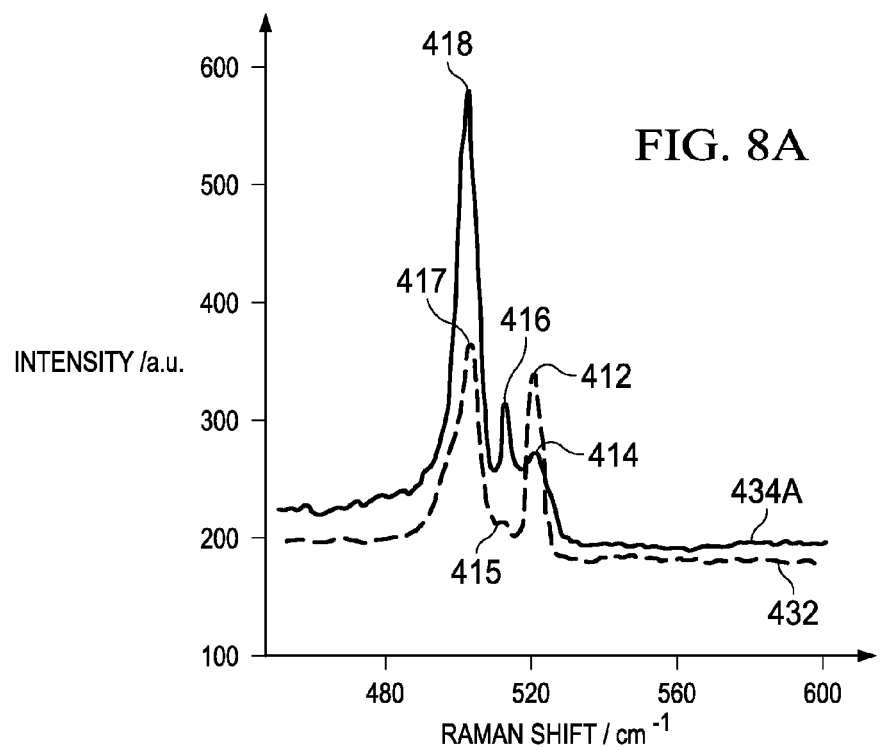
FIGS. 8A and 8B illustrate the schematic Raman spectra obtained from the sample in FIG. 7.

The Raman spectrum obtained from the first probing is illustrated in FIG. 8A in accordance with some embodiments, and is schematically illustrated as spectrum 432 in FIG. 8A. It is appreciated that depending on the structure of sample 26, the spectrum may vary. In FIG. 8A, peak 412 of spectrum 432 is the peak of bulk substrate 38, which is the reference peak for determining the stresses in the stressed regions. Peak 417 is the peak of SiGe regions 43. In some embodiments, regions 40, 43, and 45 in FIG. 7 are very shallow regions, sometimes having depths of several nanometers. Accordingly, with the laser with the first wavelength (which is relatively long) being used, the peak of strained silicon layer 45 is still too weak to be identified. For example, as shown in FIG. 8A, peak 415 of strained silicon layer 45 is difficult to be distinguished from peak 417 of SiGe regions 43. To solve this problem, a laser with a second wavelength smaller than the first wavelength is used for a second probing.

Before the second probing is started, the first probing is ended. Referring back to FIG. 1 again, multi-wavelength laser source 12 generates a second laser beam 30 having a second wavelength smaller than the first wavelength. The second wavelength is selected to have a penetration depth deeper than depth D2 in FIG. 7 and shallower than the penetration depth of the first laser beam. For example, depending on the depths D2 in FIG. 7, the second wavelength may be 363 nm or 441.6 nm. As a result, the respective Raman spectrum reflects the stress information in the regions inside strained silicon layer 45, wherein the respective Raman spectrum is illustrated as spectrum 434A in FIG. 8A. For example, assuming depth D2 (FIG. 7) is thinner than 5 nm (for example, 2 nm or 3 nm), then the lasers with wavelengths equal to or shorter than about 363.8 nm may be used to detect the stresses in regions 40, 43, and 45. If depth D2 is greater than 5 nm, then the laser with the wavelength longer than 363.8 nm is used to detect the stresses in regions 40, 43, and 45.

Figure 8B:
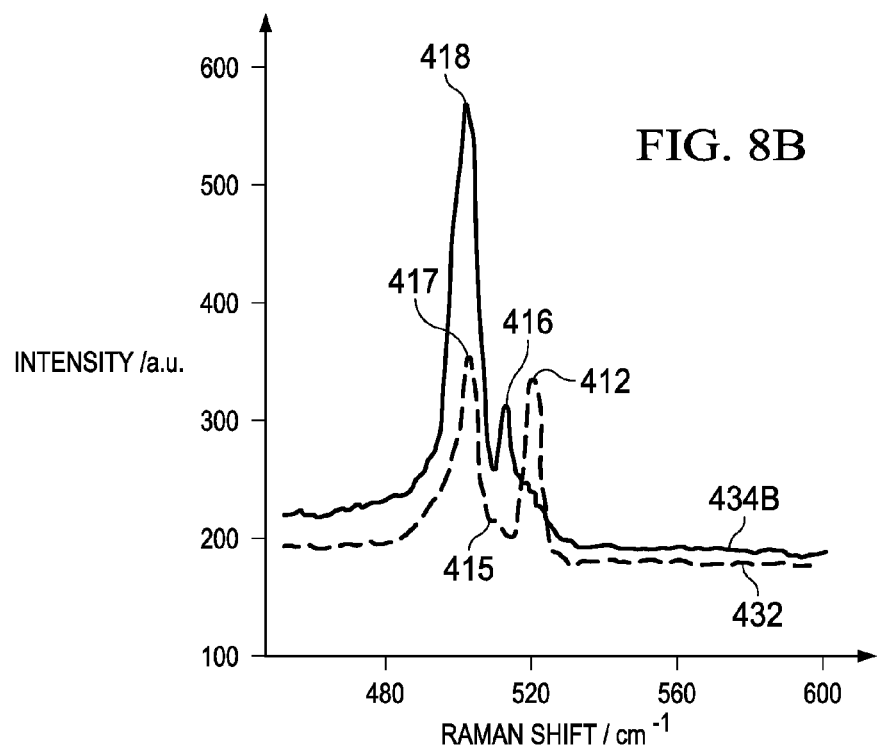

Referring to spectrum 434A in FIG. 8A, peak 414 in spectrum 434A corresponds to bulk substrate 38, which is free from stress. Peak 414 is also the reference peak. Peak 416 corresponds to strained silicon layers 45, and peak 418 corresponds to SiGe regions 43. In some embodiments, peak 414 is very low, as shown in FIG. 8A. In alternative embodiments, for example, when the second wavelength is too short and does not penetrate into the bulk substrate 38 (FIG. 7) for enough depth, there is no peak 414 that can be identified. FIG. 8B illustrates the respective spectrum 434B, in which the peak 414 in spectrum 434A (FIG. 8A) is no longer distinguishable. Accordingly, to determine the stress in strained silicon layer 45, peak 412 is needed. Referring to FIGS. 8A and 8B, by determining how much peak 416 shifts from peak 412 (and/or 414 if it can be identified), the stress in shallow regions 42, 43, and STI regions 40 can be determined using the relationship revealed by FIG. 4.

If the desirable peaks 416 and 417 are successfully obtained in the second probing, the stresses in shallow regions 42, 43, and STI regions 40 can be determined, and no more probing is required. Situation may also occur that the second wavelength is not appropriate, and hence the desirable peaks 416 and 417 (FIGS. 8A and 8B) are not shown or not clear enough. Accordingly, a third probing may be performed using a third wavelength, which may be shorter or longer than the second wavelength. For example, if it is determined that the second wavelength is too short (for example, regions 43/45 are thicker than expected due to process variation), the third wavelength is selected to be longer than the second wavelength. Conversely, if it is determined that the second wavelength is too long (for example, regions 43/45 are thinner than expected due to process variation), the third wavelength is selected to be shorter than the second wavelength.

Referring again to FIG. 1, in accordance with some embodiments, after the second probing is ended, the third probing is performed, wherein multi-wavelength laser source 12 generates a third laser beam 30 having the third wavelength different from the first and the second wavelengths. The respective spectrum may also be schematically illustrated as spectrum 434, and the details are not discussed in detail herein. After the third probing, the shift of peak 416 from peak 412/414 is used to determine the stress in the shallow regions.

Fin structures typically have small horizontal sizes such as fin width S1 and STI width S3. This requires the planar resolution of the probing to be small to be able to accurately determine the stresses in specific regions such as semiconductor regions 43 and STI regions 40 (FIG. 7). In the embodiments of the present disclosure, tip size S2 (FIG. 10) is reduced, for example, to 40 nm or smaller. This significantly improves the planar resolution in the stress measurement. With the reduction of tip size S2, the planar resolution of the TERS may be improved to close to the resolution of AFM.

Figure 9:
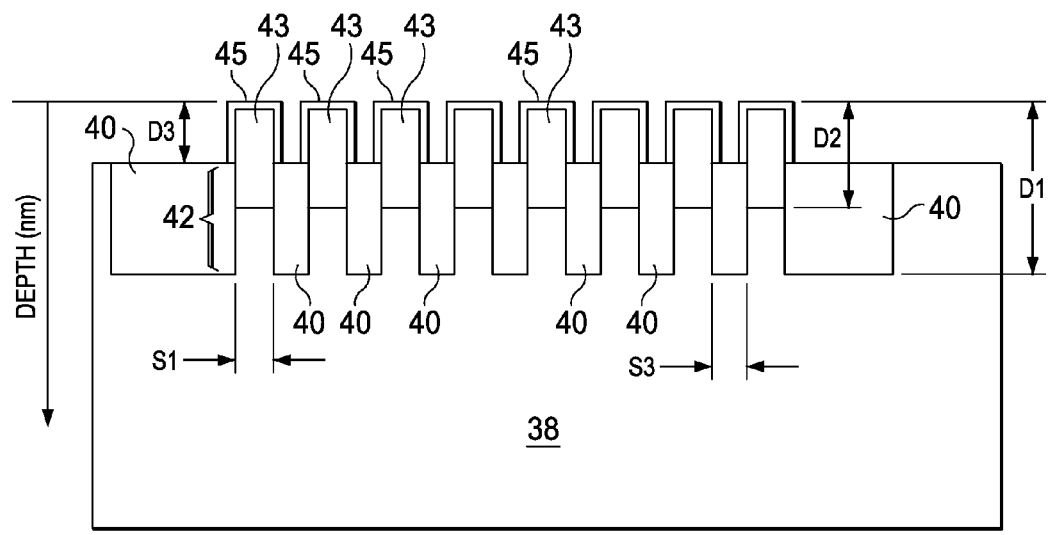
FIG. 9 illustrates a cross-sectional view of a sample integrated circuit structure in accordance with some embodiments, which includes semiconductor fins over STI regions, with the STI regions extending into a semiconductor substrate.

FIG. 9 illustrates an exemplary integrated circuit structure, whose stresses may be determined using the embodiments of the present disclosure. In FIG. 9, fins 44 include SiGe regions 43 and strained silicon layers 45 over SiGe regions 43. STI regions 40 extending into substrate 38. In FIG. 9, the stresses in strained silicon layers 45 and SiGe regions 43 may be determined in accordance with the embodiments of the present disclosure.

In the embodiments of the present disclosure, by using a laser(s) having small wavelengths, the resolution of the respective TERS probing is improved. Furthermore, shallow regions in the order of tens or hundreds of nanometers may be probed. By adopting a plurality of lasers having different wavelengths, the stresses in different depths of samples may be determined. In addition, the size of the probe tip of the AFM probe is reduced to smaller than 40 nm, so that the resolution of the probing may be improved. The chamber environment of the probing is also improved to further improve the Raman scattering signal strength.

In accordance with some embodiments, a method includes performing a first probing on a sample integrated circuit structure to generate a first Raman spectrum. During the first probing, a first laser beam having a first wavelength is projected on the sample integrated circuit structure. The method further includes performing a second probing on the sample integrated circuit structure to generate a second Raman spectrum, wherein the TERS method is used to probe the sample integrated circuit structure. During the second probing, a second laser beam having a second wavelength different from the first wavelength is projected on the sample integrated circuit structure. A stress in a first probed region of the sample integrated circuit structure is then from the first Raman spectrum and the second Raman spectrum.

In accordance with other embodiments, a method includes providing a sample integrated circuit structure. The sample integrated circuit structure includes a bulk substrate, and STI regions extending into the bulk substrate, wherein semiconductor regions are located between the STI regions. A first probing is performed on the sample integrated circuit structure to generate a first Raman spectrum. During the first probing, a first laser beam having a first wavelength is projected on the sample integrated circuit structure. A second probing is performed on the sample integrated circuit structure to generate a second Raman spectrum. During the second probing, a second laser beam having a second wavelength shorter than the first wavelength is projected on the sample integrated circuit structure. During the second probing, an AFM probe is adjacent to a surface portion of the sample integrated circuit structure projected by the second laser beam. The first Raman spectrum and the second Raman spectrum are compared to determine a stress in a probed region probed by the second probing, wherein the probed region is over bottom surfaces of the STI regions.

In accordance with yet other embodiments, an apparatus includes a multi-wavelength laser source configured to generate a plurality of laser beams having wavelengths different from each other, and an AFM probe having a probe tip, wherein the apparatus is configured to synchronize movements of the laser beam and the probe tip. The apparatus further includes a spectrometer configured to receive Raman scattering from the sample integrated circuit and to generate a Raman spectrum from the Raman scattering.

Although the embodiments and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:
1. A method comprising:
  performing a first probing on a sample integrated circuit structure to generate a first Raman spectrum, wherein during the first probing, a first laser beam having a first wavelength is projected on the sample integrated circuit structure;
  performing a second probing on the sample integrated circuit structure to generate a second Raman spectrum, wherein a Tip-Enhanced Raman Scattering (TERS) method is used to probe the sample integrated circuit structure, and wherein during the second probing, a sec- ond laser beam having a second wavelength different from the first wavelength is projected on the sample integrated circuit structure; and determining a stress in a first probed region of the sample integrated circuit structure from the first Raman spectrum and the second Raman spectrum.

2. The method of claim 1, wherein the first wavelength is in a visible-light range, and wherein the second wavelength is outside the visible-light range.

3. The method of claim 1, wherein during the first probing and the second probing, an Atomic Force Microscopy (AFM) probe is used to assist the first probing and the second probing, respectively.

4. The method of claim 3, wherein the AFM probe comprises a probe tip with a size smaller than about 40 nm.

5. The method of claim 1, wherein the sample integrated circuit structure comprises:
a bulk substrate with a neutral stress; and
Shallow Trench Isolation (STI) regions extending into the bulk substrate, wherein a second penetration depth of the second laser beam is shallower than bottoms of the STI regions.

6. The method of claim 1 further comprising:
performing a third probing on the sample integrated circuit structure to generate a third Raman spectrum, wherein the TERS method is used to probe the sample integrated circuit structure, and wherein during the third probing, a third laser beam having a third wavelength different from the first wavelength and the second wavelength is projected on the sample integrated circuit structure.

7. The method of claim 1, wherein during the first probing and the second probing, a chamber holding the sample integrated circuit structure is filled with an inert gas or in vacuum.

8. A method comprising:
providing a sample integrated circuit structure, wherein the sample integrated circuit structure comprises:
a bulk substrate; and
Shallow Trench Isolation (STI) regions extending into the bulk substrate, wherein semiconductor regions are located between the STI regions;
performing a first probing on the sample integrated circuit structure to generate a first Raman spectrum, wherein during the first probing, a first laser beam having a first wavelength is projected on the sample integrated circuit structure;
performing a second probing on the sample integrated circuit structure to generate a second Raman spectrum, wherein during the second probing, a second laser beam having a second wavelength shorter than the first wavelength is projected on the sample integrated circuit structure, and wherein during the second probing, an Atomic Force Microscopy (AFM) probe is adjacent to a surface portion of the sample integrated circuit structure projected by the second laser beam; and
comparing the first Raman spectrum and the second Raman spectrum to determine a stress in a first probed region probed by the second probing, wherein the first probed region is over bottom surfaces of the STI regions.

9. The method of claim 8, wherein the sample integrated circuit structure further comprises semiconductor fins over top surfaces of the STI regions, and wherein the first probed region of the sample integrated circuit structure has a bottom level with or higher than bottom surfaces of the semiconductor fins.

10. The method of claim 8, wherein the first probed region of the sample integrated circuit structure comprises portions of semiconductor regions between neighboring ones of the STI regions.

11. The method of claim 8, wherein the first wavelength is in a visible light range, and wherein the second wavelength is in an ultraviolet light range.

12. The method of claim 8, wherein the AFM probe comprises a probe tip with a size smaller than about 40 nm.

13. The method of claim 8 further comprising:
performing a third probing on the sample integrated circuit structure to generate a third Raman spectrum, wherein during the third probing, a third laser beam having a third wavelength different from the first wavelength and the second wavelength is projected on the sample integrated circuit structure.

14. The method of claim 8, wherein during the first probing and the second probing, a chamber holding the sample integrated circuit structure is filled with an inert gas or in vacuum.

15. A method comprising:
performing a first probing on a sample integrated circuit structure to generate a first Raman spectrum, wherein during the first probing, a first laser beam having a first wavelength is projected on the sample integrated circuit structure, wherein the first wavelength is in a visible-light range;
performing a second probing on the sample integrated circuit structure to generate a second Raman spectrum, wherein a Tip-Enhanced Raman Scattering (TERS) method is used to probe the sample integrated circuit structure, and wherein during the second probing, a second laser beam having a second wavelength different from the first wavelength is projected on the sample integrated circuit structure, with the second wavelength being outside of the visible-light range; and
determining a stress in a first probed region of the sample integrated circuit structure by comparing the first Raman spectrum and the second Raman spectrum.

16. The method of claim 15, wherein during the first probing and the second probing, an Atomic Force Microscopy (AFM) probe is used to assist the first probing and the second probing, respectively.

17. The method of claim 16, wherein the AFM probe comprises a probe tip with a size smaller than about 40 nm.

18. The method of claim 15, wherein the sample integrated circuit structure comprises:
a bulk substrate with a neutral stress; and
Shallow Trench Isolation (STI) regions extending into the bulk substrate, wherein a second penetration depth of the second laser beam is shallower than bottoms of the STI regions.

19. The method of claim 15 further comprising:
performing a third probing on the sample integrated circuit structure to generate a third Raman spectrum, wherein the TERS method is used to probe the sample integrated circuit structure, and wherein during the third probing, a third laser beam having a third wavelength different from the first wavelength and the second wavelength is projected on the sample integrated circuit structure.

20. The method of claim 15, wherein during the first probing and the second probing, a chamber holding the sample integrated circuit structure is filled with an inert gas or in vacuum.

* * * * *